(12) United States Patent
Fox et al.

(10) Patent No.: US 6,586,181 B1
(45) Date of Patent: Jul. 1, 2003

(54) METHOD FOR DETECTING ALLELIC IMBALANCE

(75) Inventors: Jayne C Fox, Macclesfield (GB); Kemal Haque, Northwich (GB); Stephen Little, Northwich (GB)

(73) Assignee: Syngenta Limited, London (GB)

( * ) Notice: Subject to any disclaimer, the term of this patent is extended or adjusted under 35 U.S.C. 154(b) by 0 days.

(21) Appl. No.: 09/673,465

(22) PCT Filed: Apr. 13, 1999

(86) PCT No.: PCT/GB99/01121

§ 371 (c)(1),
(2), (4) Date: Oct. 17, 2000

(87) PCT Pub. No.: WO99/54498

PCT Pub. Date: Oct. 28, 1999

(30) Foreign Application Priority Data

Apr. 17, 1998 (GB) .............................................. 9808145

(51) Int. Cl.[7] .......................... C12Q 1/68; C12P 19/34; C07H 21/04; C07H 21/00

(52) U.S. Cl. ........................ 435/6; 435/91.1; 435/91.2; 536/23.1; 536/24.3; 536/24.32; 536/24.33; 536/25.4; 210/600

(58) Field of Search .............................. 435/6, 5, 91.1, 435/91.2, 196, 810; 536/23.1, 24.3, 24.32, 24.33, 25.4; 210/600

(56) References Cited

U.S. PATENT DOCUMENTS

| | | | |
|---|---|---|---|
| 5,210,015 A | * | 5/1993 | Gelfand et al. ................ 435/6 |
| 5,750,335 A | * | 5/1998 | Gifford ........................... 435/6 |
| 5,795,976 A | | 8/1998 | Oefner et al. |
| 5,811,239 A | | 9/1998 | Frayne |
| 5,824,471 A | | 10/1998 | Marshal et al. |
| 5,827,648 A | * | 10/1998 | Eastman et al. ............... 435/5 |

OTHER PUBLICATIONS

O'Donovan et al., "Blind Analysis of Denaturing High–Performance Liquid Chromatography as a Tool for Mutation Detection", GENOMICS, 1998, vol. 52, pp. 44–49, Article No. GE985411.

Riblet, Breast Cancer Genes Identified by Loss of Heterozygosity, Report prepared by Medical Biology Institute, May, 1997, Report No. L980915, pp. 1, 3–8.

* cited by examiner

*Primary Examiner*—Kenneth R. Horlick
*Assistant Examiner*—Cynthia Wilder
(74) *Attorney, Agent, or Firm*—Ropes & Gray (57) ABSTRACT

A method for detecting allelic imbalance (AI) in sample nucleic acid, which method comprises providing multiple copies of a target nucleic acid region present in the sample, the target nucleic acid region comprising a marker of heterozygosity, separating the multiple copies into individual strands then allowing the individual strands to reanneal under conditions which permit the formation of homoduplexes and heteroduplexes, removing any heteroduplexes so formed, subjecting the remaining homoduplexes to the above steps of separation, reannealing and heteroduplex removal one or more times so that any difference in the initial ratio of allelic variants is amplified, and detecting the presence or absence of AI by reference to any difference in allele ratio so detected.

18 Claims, 5 Drawing Sheets

METHOD FOR DETECTING ALLELIC IMBALANCE

This invention relates to a diagnostic method for detecting genetic changes associated, inter alia, with the development of cancer. The method detects allelic imbalance (AI), such as loss of heterozygosity (LOH), in nucleic acid from an individual and can be applied to samples in which only a small proportion of the cells display AI, thereby allowing the early identification of mutations which lead to the progression of cancer. The invention also relates to amplification primers for use in the method and to diagnostic kits containing them.

The term "allelic imbalance" refers to the chromosomal loss or gain of a region of a chromosome when the partner chromosome (in a diploid cell) is unaltered. Allelic imbalance is typically found in tumour cells. Allelic imbalance may be due to selective loss of a region of DNA derived from a single chromosome and is referred to as loss of heterozygosity (LOH) when the partner chromosome is varied in some form, most commonly by microsatellite size. Other causes of AI include: gene amplification (i.e. myc oncogene may be amplified 5–10 fold), heteroplasmy or, at the transcript level, differential allelic expression (i.e. maternal allele vs paternal allele).

Heteroplasmy most commonly refers to imbalanced ratios of maternal mitochondrial DNA and may be associated with specific pathogenic effects. The phenotype is dependent not just on homo/heterozygosity, but the relative frequencies of both "alleles". The inheritance of allele sequences does not occur in a Mendelian manner, and the ratio of maternal "mutant" and maternal "WT" alleles can vary between tissue/cell types. Heteroplasmy may be involved in a wide range of pathological conditions (eg mitochondrial, cardiac and encephalic myopathies) including a possible role in the pathology of Parkinson's and Alzheimer's disease (Suomalainen A, Annals of Medicine. 29:235–246, 1997).

Loss of a particular region of a chromosome is a frequent event in the development and progression of cancer. Different types of tumour have been found to exhibit loss of different chromosomal regions, strongly suggesting that the regions contain genes which are essential for the prevention of neoplasia. These genes, called tumour suppressor genes, function primarily in the regulation of the cell cycle. Inactivation of tumour suppressor genes is believed to be one of the earliest cellular events which lead to the development of cancer.

Identification of genetic changes involved in the development of cancer is a promising area for the early diagnosis of the disease, and improved techniques for detecting these genetic changes are required.

The loss of one variant form of the two copies of a given DNA, or potentially, transcribed RNA sequence, normally present in diploid cells is defined herein as loss of heterozygosity (LOH). LOH reflects part of the process which ultimately results in the inactivation of tumour suppressor genes. Somatic mutation, defined herein as acquired small DNA sequence changes such as point mutation, small insertions or deletions, frequently results in the inactivation of the remaining functional allele.

Detection of such alterations in nucleic acid sequence may be difficult for two reasons. Firstly, the affected cells may be very rare within the tissue sample of interest. Secondly, the exact position of the mutation within this sequence of interest may not easily be predicted, thus requiring detailed and time consuming analysis, a process incompatible with the development of a reliable and cost effective diagnostic test. Although several techniques have been used to detect LOH as a diagnostic indicator of cancer, available methods suffer from a number of disadvantages and generally lack sensitivity. As a consequence, there is a significant need for more sensitive methods for the identification of somatic nucleic acid sequence changes.

A fundamental requirement for any method to detect AI is a procedure to distinguish between the two alleles (chromosomal regions of interest) within a cell. Techniques to achieve this fall into two main categories, cytogenetic and molecular.

Cytogenetic techniques directly visualise, by microscopy based techniques, the loss of a chromosome or a chromosomal region within a cell. A normal cell should contain two copies of each autosome one of maternal origin and one of paternal origin. The principal requirement to detect AI (such as LOH) cytogenetically is a probe which will specifically hybridise to the particular chromosome or region of interest. The identification of AI is achieved by counting the number of signals associated with each nucleus using microscopy.

In contrast, molecular techniques analyse a population of cells and require a probe or marker which differs between the maternal and paternal alleles. Traditionally, microsatellite markers have been used for this purpose. As long as a chromosome pair differs in the number of repeat units at the relevant microsatellite then loss of one of the chromosomes is indicated by loss of a microsatellite of the appropriate size.

With AI detection, in a situation where all of the cells in the sample to be analysed contain the alteration then the analysis is fairly straightforward, with the proviso that the region of interest is either large enough to allow cytogenetic analysis or appropriate sequence information is available for molecular analysis. Indeed, with substantially homogeneous populations of tumour cells, simple one round heteroduplex analysis has been proposed as a means of detecting the LOH at tumour suppressor gene loci (Mansukhani et al (1997, Diag. Mol. Pathol., 6, 229–237). However, AI analysis is much more difficult in mixed samples, i.e. those in which only a proportion of the cells comprising the sample display AI. For example, if only 5% of the cells in a population display LOH of, say the maternal allele, then the ratio of paternal to maternal alleles in the sample would be 51:49. It is often the case that the clinical samples available for analysis in cancer diagnosis are not homogeneous and the proportion of cells containing any given mutation can vary from 100% to less than 1%.

Existing techniques are not well suited to LOH analysis in mixed populations. Although cytogenetic techniques have the potential to detect LOH in a small proportion of a sample, in practice they are technically difficult and not well developed to routine clinical use, and are limited to the detection of relatively large sequence changes. Currently available molecular techniques are more amenable to clinical application but they are not able to detect small changes in the relative level of maternal to paternal alleles within an under represented population. Mansukhani et al (1997, Diag. Mol. Pathol., 6, 229–237) developed a method based on the formation of heteroduplexes between PCR amplified alleles which could be used to identify recurrent mutations in the BRCA1 and BRCA2 genes. However, the analytical sensitivity of the method was very low, severely limiting its use in clinical diagnosis. Indeed, the authors report that use of heteroduplex analysis for detecting the loss of the remaining allele is only possible if the sample contains no more than 3–10% normal issue.

Similarly, the sensitivity of other currently available molecular techniques (i.e. microsatellite LOH analysis) is such that when the rarer population, i.e. the population with LOH, is less than about 25% of the total sample, LOH is not easily detectable.

Denaturing high performance liquid chromatography (DHPLC) has been shown recently to be a useful method for detecting single nucleotide polymorphisms and inherited mutations by detecting heteroduplex DNA (Liu et al. Nucleic Acids Research. 26(6):1396–1400, 1998; O'Donovan et al. Genomics 52:44–49, 1998). U.S. Pat. No. 5,795,976 also discloses a method for separating heteroduplex and homoduplex molecules in a mixture using high performance liquid chromatography. Separation of heteroduplexes and homoduplexes by DHPLC is particularly useful in the method of the present invention.

The present invention is a novel molecular technique which can detect AI in nucleic acid from an individual by measuring the change in the ratio of allelic variants (of maternal or paternal origin for example) after one or more rounds of heteroduplex formation and removal. The method of the invention amplifies the initial difference between the levels of allelic variants, greatly increasing the sensitivity of the assay. The method can thus be used to detect allelic imbalance when only a small proportion of the cells have mutated, allowing early identification of the genetic changes which lead to the development of cancer.

Therefore in a first aspect of the invention we provide a method for detecting allelic imbalance (AI) in sample nucleic acid, which method comprises providing multiple copies of a target nucleic acid region present in the sample, the target nucleic acid region comprising a marker of heterozygosity, separating the multiple copies into individual strands then allowing the individual strands to reanneal under conditions which permit the formation of homoduplexes and heteroduplexes, removing any heteroduplexes so formed, subjecting the remaining homoduplexes to the above steps of separation, reannealing and heteroduplex removal one or more times so that any difference in the initial ratio of allelic variants is amplified, and detecting the presence or absence of AI by reference to any difference in allele ratio so detected.

The method of the invention enhances AI detection by amplifying the difference between the levels of variant forms derived from maternal and paternal chromosomes, or in the case of heteroplasmy the relative ratio of maternally inherited mitochondrial DNA, in the sample. This is achieved by first allowing molecules derived from each allelic variant to anneal to each other and then using a technique which will remove heteroduplexes formed from the annealing of the nucleic acid derived from both alleles. By repeating the process of heteroduplex formation and removal one or more times, the net effect is to steadily enrich (in relative not absolute levels) the sample for whichever allele is over-represented in the original nucleic acid population.

At the start of the process the levels of the two alleles may differ only slightly but for example, after several rounds of enrichment the allele which was slightly over-represented at the start of the process may form >95% of the total. By measuring the change in the ratio of the variant alleles during the enrichment procedure, the level of AI in the original sample can be determined.

Conveniently, the enrichment cycle of strand separation, reannealing and heteroduplex removal will be repeated 1–15 times. In a preferred aspect of the invention, the enrichment cycle will be repeated 2–10 times and in a most preferred aspect of the invention the enrichment cycle will be repeated 3–5 times.

The method of the invention uses any suitable difference between the variant alleles (i.e. between the maternal and paternal alleles) which can unambiguously differentiate between the two chromosomal regions but will still allow heteroduplexes to form between them. This difference in nucleotide sequence is often referred to as a marker of heterozygosity. Ideally, the sequence change is a polymorphism which may take the form of a single nucleotide difference or a small insertion or deletion, for example 1–10 nucleotides in length.

Allelic imbalance may be used as a marker for acquired DNA changes which underlie tumour formation. The method of the invention is therefore particularly useful in cancer management, including diagnosis, pre-symptomatic disease detection (screening), molecular staging and therapy monitoring.

A preferred target region of interest is the APC gene (adenomatous polyposis coli gene) located on chromosome 5q (5q21), a tumour suppressor gene which has been strongly implicated in the development of colorectal cancer. Other preferred regions of interest are the DCC gene (deleted in colorectal cancer gene) located on chromosome 18q; the tumour suppressor gene p53 located on chromosome 17p (17p13); the mannose 6-phosphate/insulin-like growth factor 2 receptor tumour suppressor gene located on chromosome 6q (6q26–27), (see Oates et al., Breast Cancer Res Treat. 47(3):269–81, 1998 and De Souza et al., Oncogene.10(9):1725–1729, 1995); and the tumour suppressor gene p16 located on chromosome 9p (9p21). Table 1 provides a non-comprehensive list of tumour suppressor genes, their chromosomal locations and types of tumours associated with AI to the genes. Mutations within these genes or at these chromosomal locations have been well documented. AI amongst these and other tumour suppressor genes can be detected using the method described herein.

A particularly preferred target region of interest is the region of human chromosome 10q bounded by DNA defined by the markers D10S541 and D10S215, which contains the tumour suppressor gene PTEN (PCT Application WO97/15686, Imperial Cancer Research Technology Ltd.).

TABLE 1

| Tumour Suppressor Gene | Chromosomal Location | Tumour Types Observed |
|---|---|---|
| P53 | 17p13 | brain tumours, sarcomas, leukemia, breast cancer |
| APC | 5q21 | colon cancer |
| BRCA1 | 17q21 | breast and ovarian cancer |
| BRCA2 | 13q12.3 | breast and ovarian cancer |
| NF1 (neurofibromin 1) | 17q11.2 | neurofibromas, gliomas, sarcomas |
| NF2 merlin or neurofibromin 2 | 22q12.2 | Schwann cell tumours, astrocytomas, meningiomas, ependymonas |
| DPC4 also known as Smad4 | 18q21.1 | pancreatic carcinoma, colon cancer |
| TSC1 hamartin | 9q34 | facial angiofibromas |
| TSC2 tuberin | 16 | benign growths (hamartomas) in many tissues, astrocytomas, rhabdomyosarcomas |
| MEN1 | 11q13 | parathyroid and pituitary adenomas, islet cell tumours, |
| RB1 | 13q14 | retinoblastoma, osteogenic sarcoma |
| WT1 | 11p13 | pediatric kidney cancer |
| MSH2 | 2p16 | colon cancer |
| MLH1 | 3p21 | colon cancer |
| VHL | 3p26–p25 | renal cancers, hemangioblastomas, pheochromocytoma |

TABLE 1-continued

| Tumour Suppressor Gene | Chromosomal Location | Tumour Types Observed |
|---|---|---|
| CDKN2A cyclin-dependent kinase inhibitor 2A | 9p21 | melanoma, pancreatic cancer, others |
| PTCH patched | 9q22.3 | basal cell skin cancer |

As mentioned above, another cause of AI is amplification, particularly of oncogenes. Amplification represents one of the major molecular pathways through which the oncogenic potential of proto-oncogenes is activated during tumourigenesis (Schwab. BioEssays. 20:473–79, 1998). The following are examples of proto-oncogenes that are often amplified resulting in AI, and thus (provided they contain a marker of heterozygosity), are detectable according to he method of this invention: MYC, ABL, $RAS_K$, $RAS_W$, MYB, ERBA, ERBB2 (also known as HER2 or NEU), MYCN and MYCL (see Schwab & Amler. Genes Chromosom. Cancer. 1:181–193, 1990; and Schwab. BioEssays. 20:473–479, 1998).

AI is detected in nucleic acid extracted from a clinical tissue or fluid specimen by measuring the change in the ratio of inherited alleles after one or more rounds of heteroduplex formation and removal. The invention therefore provides a method for detecting AI in nucleic acid extracted from a clinical sample, comprising providing multiple copies of a target nucleic acid region present in the sample, the target region comprising a marker of heterozygosity, and measuring the change in the ratio of allelic variants of said marker of heterozygosity after one or more rounds of heteroduplex formation and removal.

The sample nucleic acid from an individual may be either genomic DNA or cDNA generated from mRNA by reverse transcription. The sample nucleic acid is preferably one isolated from an animal, preferably a human tissue or fluid sample. Such a sample may conveniently be from a solid tissue, such as from a tumour or tumour margin, or other biopsy sample, or from a stool sample or bodily fluid sample (such as, sputum, saliva, blood, semen, urine and the like). The sample may be fresh or one preserved by for example, freezing, formalin, or other tissue fixation methods, and may then optionally be embedded in paraffin or the like. The sample nucleic acid may be one indirectly obtainable from the sample, i.e. one prepared by amplification (such as PCR) from the original sample.

Multiple copies of the target region of interest containing a marker of heterozygosity can be obtained by amplification or any convenient enrichment procedure.

Amplification of the target region of interest may be achieved using any convenient technique such as the polymerase chain reaction (PCR) (U.S. Pat. Nos. 4,683,195 and 4,683,202 Roche). The method of the invention can be used to separate and detect the existence of a single base mismatch in a DNA duplex containing up to about 2000 base pairs. The preferred length of target DNA region is between 30 and 1000 bp, more preferably between 50 and 500, most preferably between 100 and 150 bp. Because clinical tissue specimens such as paraffin embedded tissue biopsies are often found to be partially degraded, it can be technically difficult to amplify large fragments. Consequently, amplified PCR products from such samples should preferably be about 50–250 bp in size. Most preferably, the amplified PCR products should be about 100–150 bp in size. However, future development of improved clinical procedures for sampling and preserving tissue specimens may be expected to relax this size restriction and there is believed to be no theoretical limit to the preferred size range of the amplified products.

Other procedures which may conveniently be used to enrich the region of interest include magnetic Dynabeads (Dynal®, Norway) or DARAS® capture probe cartridges (Tepnel Life Sciences Ltd., UK).

With DHPLC separation of the molecular species (heteroduplex and homoduplex) no prior purification of the two molecular species would be required as unincorporated amplification reaction components (e.g. primers) would be eluted in different fractions. With other separation techniques, such as enzymatic, the amplified regions of interest may optionally be purified by any convenient method. A preferred method of purification is to degrade any remaining, unincorporated amplification primers by treatment with exonuclease I.

Duplexes are formed by separating and reannealing the amplified regions of interest. Typically, this will be achieved by heat denaturing a solution containing the amplified regions of interest, followed by cooling to allow the melted DNA strands to reanneal. However, it is not intended that the method of the invention should be restricted to thermal techniques, and any convenient method for duplex separation and formation may be used.

Heat denaturation is conveniently carried out by subjecting the nucleic acid sample to temperatures around 95° C., for example between 92° C. and 100° C., for a duration sufficient to ensure strand separation, nominally at least 1 minute, usually between 2 and 10 minutes. Annealing is generally carried out by allowing the temperature of the denatured solution to drop to 37° C. over a period of 1 to 2 min. A more gradual cooling rate of 1–4° C. per minute may be preferred. The optimum denaturing temperature and annealing rate will depend on the duplex composition and length. The optimum temperatures and times required to ensure denaturation and annealing can be determined by the person skilled in the art.

The method assumes that the relative number of heteroduplexes and homoduplexes formed will depend only on the relative frequency of the two alleles. In practice, it is possible that homoduplexes may form in preference to heteroduplexes because of the greater binding affinity of the perfectly matched sequences. The introduction of a thermostable region into the product so that any potential annealing bias due to the mismatch will be overpowered by the thermostable region should ensure random annealing of nucleic acid molecules. Therefore, in a preferred aspect of the invention the method will incorporate a technique to promote the formation of stable heteroduplexes. For example, a GC clamping sequence may be incorporated into the design of the PCR primers used to amplify the nucleic acid regions of interest. Also, allelic variants of minimal primary sequence difference may be preferential to large primary sequence differences. Single nucleotide polymorphisms are preferred as these will have the least influence on heteroduplex formation.

Heteroduplexes may be removed from the reaction mixture by any convenient method, for example, physical, enzymatic or chemical mismatch cleavage, or mismatch binding.

In a preferred aspect of the invention, heteroduplexes are removed by binding to prokaryotic or eukaryotic mismatch binding proteins. An example is MutS, a mismatch binding protein isolated from E. coli, which recognises regions of double-stranded DNA containing a single mismatched base pair (Wagner el al., 1995, Nucleic Acids Research, 22, 1541–1547). MutS is allowed to bind to the heteroduplexes and bound heteroduplex/MutS complexes are removed from the reaction mixture using, for example, powdered nitrocellulose. A convenient alternative is to use MutS conjugated to magnetic beads, allowing bound heteroduplexes to be removed from the reaction mixture with a magnet. MutS may also be conjugated to biotin and the bound heteroduplexes removed from the mixture using streptavidin coated beads.

In another preferred aspect of the invention mammalian or bacterial endonucleases are used to recognise and cleave the heteroduplexes at mismatched bases (see U.S. Pat. No. 5,824,4710). Examples of preferred enzymes include bacteriophage resolvases such as T4 endonuclease VII or T7 endonuclease I. In a particularly preferred aspect of the invention, thermostable cleavage enzymes would be used in order to avoid the necessity of adding fresh enzyme during each round of heteroduplex formation and removal.

The most preferred method of separating the heteroduplex and homoduplex molecules involves physical separation, such as achieved by chromatography or electrophoresis. Suitable examples include, denaturing high performance liquid chromatography (DHPLC) and chemical or temperature denaturing electrophoresis. Denaturing HPLC is a chromatographic technique capable of separating heteroduplex and homoduplex DNA molecules in a mixture. The mixture is applied to a stationary reverse-phase support and the homo and heteroduplex molecules are eluted (under thermal or chemical conditions capable of partially denaturing heteroduplexes) with a mobile phase containing an ion-pairing reagent (e.g. triethylammonium acetate; TEAA) and an organic solvent (e.g. acetonitrile; AcN). DHPLC can also allow the direct quantitation of relative homoduplex and heteroduplex concentrations by the detection of ultraviolet absorbance or fluorescent emission of/from the separated species. The area under the absorbance/emission peak is proportional to the amount of product which therefore allows quantitative assessment of the relative proportions of each allele. DHPLC is described in Liu W et al. (Nucleic Acids Research. 26:1396–1400, 1998 and O'Donovan MC et al. Genomics. 52:4449, 1998).

A preferred method for use in the instant invention to separate heteroduplex and homoduplex molecules is as described in U.S. Pat. No. 5,795,976, incorporated herein by reference.

As mentioned above, certain physical separation techniques allow direct quantitation of the amounts of heteroduplexes and homoduplexes present after each round of separation annealing and heteroduplex removal. Quantitation of the relative frequency of the aa and bb homoduplexes remaining in the mixture after heteroduplex removal can also be analysed using any convenient mutation quantification technique.

One method is to take samples of the solution containing the homoduplexes and measure the ratio of the two alleles by PCR/ELISA using allele specific PCR primers end-labelled with haptens such as digoxigenin and dinitrophenol.

In a preferred aspect of the invention, analysis of homoduplex ratio is carried out using real-time PCR, comprising a detection system such as Molecular Beacons (as described in WO95/13399) or Scorpions™ (as described in PCT/GB98/03521, Zeneca Ltd).

In a particularly preferred aspect of the invention, analysis of homoduplex ratio is carried out using real-time ARMS™ allele specific amplification (as described in EP-0332435, Zeneca Ltd).

For any given mixture of two distinct alleles a and b, the relative frequency of homoduplex (aa and bb) and heteroduplex (ab) formation after denaturing and reannealing is defined by the equation:

$$a^2+2ab+b^2=1$$

where a frequency of allele a, b=frequency of allele b $a^2$=frequency of aa homoduplex $b^2$=frequency of the bb homoduplex 2ab=frequency of ab/ba heteroduplex For example, if each allele is initially present at equal frequency, i.e. ratio of a:b is 0.5:0.5, then the relative frequency of homoduplexes and heteroduplexes after a single round of denaturing and reannealing is $$0.5^2+2(0.5\ 0.5)+0.5^2=1$$

$$0.25+0.5+0.25=1$$

In other words, homoduplexes and heteroduplexes are formed in the ratio aa:ab:bb of 1:2:1.

Figure 1:
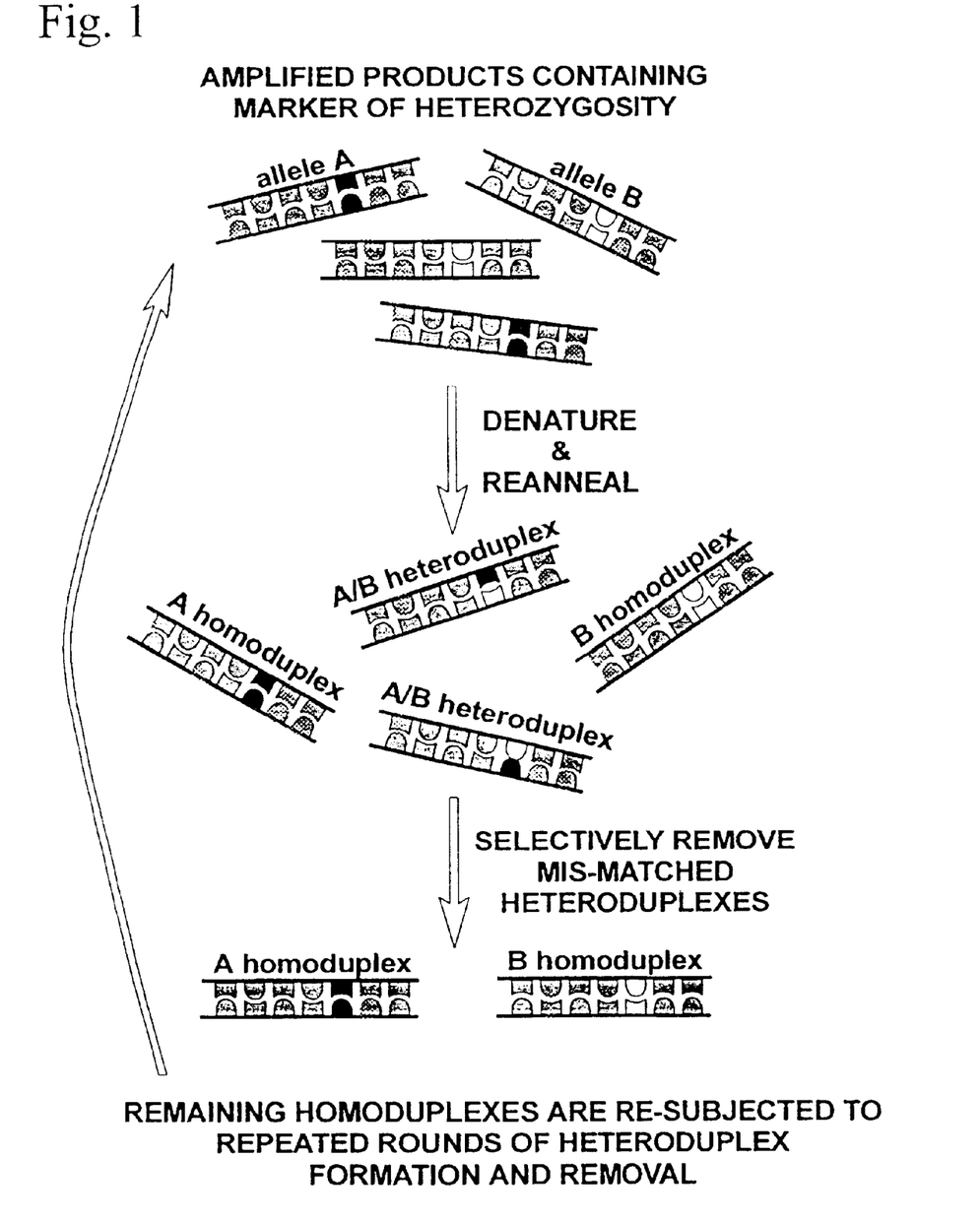
FIG. 1 shows the formation and selective depletion of mismatched allelic heterozygotes. The diagram illustrates the method of the invention involving iterative denaturing, annealing and heteroduplex removal.
Figure 2:
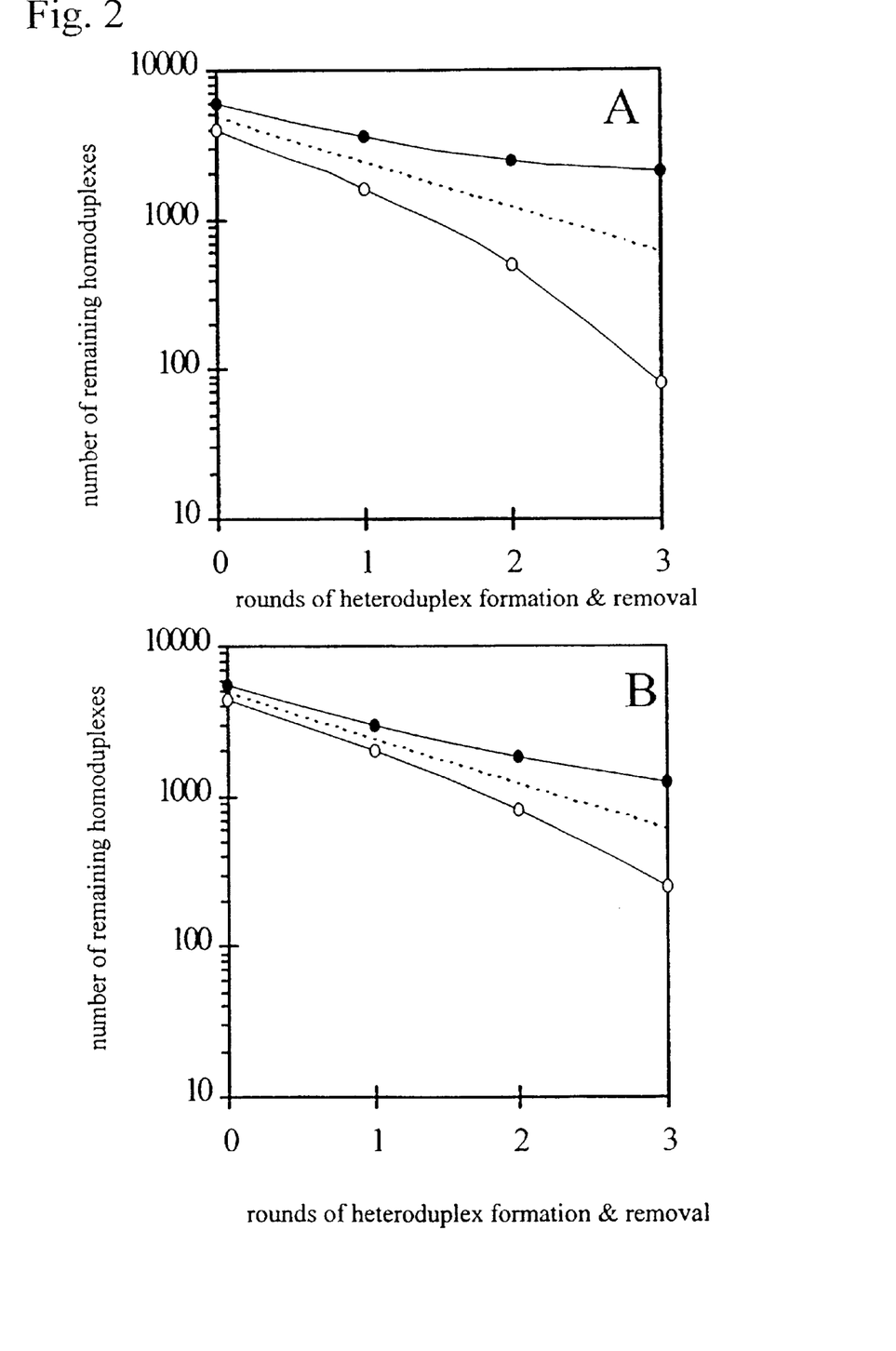
FIG. 2 demonstrates the theoretical effect of successive rounds of heteroduplex formation and removal in two individuals, one of whom displays an initial allele frequency (aa:bb) of 0.4:0.6 (FIG. 2A), and the other an initial allele frequency (aa:bb) of 0.45:0.55 (FIG. 2B).

If alleles a and b are present at exactly equivalent frequencies the ratio of a to b will remain unchanged after any number of rounds of heteroduplex formation and removal. If however, one allele is under-represented, reflecting AI, such as LOH, then the rarer allele (a) will become increasingly less representative of the total DNA population in relation to the more frequent allele (b) with successive rounds of heteroduplex formation and removal. Therefore, the ratio of aa:bb will gradually decrease after each cycle of heteroduplex formation and removal (See Table 2 and graphical representation in FIG. 2).

TABLE 2

The effect of repeated rounds of allele keteroduplex formation & removal
The equation described above was used to predict the effect of repeated heteroduplex (het-duplex) formation and removal on a population of $10^5$ alleles when initial allele frequencies are: aa & bb = 0.5 [1]; aa = 0.4 & bb = 0.6 [2]; and aa = 0.45 & bb = 0.55 [3].
This has been graphically represented in FIG. 2.

| | [1] | | | [2] | | | [3] | | |
|---|---|---|---|---|---|---|---|---|---|
| | aa | ab | bb | aa | ab | bb | aa | ab | bb |
| pre-1st het-duplex formation | | | | | | | | | |
| number of alleles | 5000 | | 5000 | 4000 | | 6000 | 4500 | | 5500 |
| frequency | 0.5 | | 0.5 | 0.4 | | 0.6 | 0.45 | | 0.55 |
| post-1st het-duplex formation | | | | | | | | | |
| number of alleles | 2500 | 5000 | 2500 | 1600 | 4800 | 3600 | 2025 | 4950 | 3025 |
| frequency | 0.25 | 0.5 | 0.25 | 0.16 | 0.48 | 0.36 | 0.203 | 0.495 | 0.303 |

TABLE 2-continued

The effect of repeated rounds of allele keteroduplex formation & removal
The equation described above was used to predict the effect of repeated heteroduplex (het-duplex) formation and removal on a population of $10^5$ alleles when initial allele frequencies are: aa & bb = 0.5 [1]; aa = 0.4 & bb = 0.6 [2]; and aa = 0.45 & bb = 0.55 [3].
This has been graphically represented in FIG. 2.

| | [1] | | | [2] | | | [3] | | |
|---|---|---|---|---|---|---|---|---|---|
| | aa | ab | bb | aa | ab | bb | aa | ab | bb |
| pre-2$^{nd}$ het-duplex formation | | | | | | | | | |
| number of alleles | 2500 | | 2500 | 1600 | | 3600 | 2025 | | 3025 |
| frequency | 0.5 | | 0.5 | 0.308 | | 0.692 | 0.401 | | 0.599 |
| post-2$^{nd}$ het-duplex formation | | | | | | | | | |
| number of alleles | 1250 | 2500 | 1250 | 493 | 2217 | 2490 | 812 | 2424 | 1812 |
| frequency | 0.25 | 0.5 | 0.25 | 0.095 | 0.426 | 0.479 | 0.161 | 0.48 | 0.359 |
| pre-3$^{rd}$ het-duplex formation | | | | | | | | | |
| number of alleles | 1250 | | 1250 | 493 | | 2490 | 812 | | 1812 |
| frequency | 0.5 | | 0.5 | 0.165 | | 0.835 | 0.309 | | 0.691 |
| post-3$^{rd}$ het-duplex formation | | | | | | | | | |
| number of alleles | 625 | 1250 | 625 | 81 | 823 | 2080 | 250 | 1121 | 1252 |
| frequency | 0.25 | 0.5 | 0.25 | 0.027 | 0.276 | 0.697 | 0.095 | 0.427 | 0.477 |

The rate at which the ratio of aa:bb changes with successive rounds of heteroduplex formation and removal is governed by the initial aa:bb ratio in the original sample, so that even though the initial difference was too small to measure accurately, the amplified difference can be easily detected.

By plotting the rate of change of the aa:bb ratio and extrapolating backwards, the method provides an estimate of the level of AI in the original sample. In principle this technique should be able to detect AI when the difference in frequency of the two alleles is <1%.

The following calculation demonstrates how the initial frequency of maternal and paternal alleles may be calculated for a clinical tissue specimen in which, for example, 5% of the cells display AI:

Consider a tissue sample in which 5% of the cells are tumour cells which display AI. The tissue sample will comprise 95% normal cells containing alleles a and b, and 5% tumour cells containing only allele b as a result of AI. Assume for the sake of argument, that the total number of cells present in the sample is 1000 cells. The normal cells will contain 950 a alleles and 950 b alleles and the tumour cells will contain 50 b alleles only. Thus the total number of b alleles in the sample is 1000 and the total number of a alleles in the sample is 950. The relative frequency of the two alleles (a:b) is thus 950:1000 which (after normalising by multiplying both sides by 1000/1950) is equivalent to a percentage frequency ratio of 49:51.

The present method requires individuals to be heterozygous at a polymorphic marker within the region of interest. Individuals will therefore have to be typed for the existence of heterozygosity within the test genetic locus. Such typing could of course be done using DHPLC analysis, or any other convenient method. In order to identify markers of heterozygosity at a locus in the region suspected of AI the target region of interest is analysed for allelic variation using a source of nucleic acid unaffected by AI. The source of nucleic acid is conveniently a blood sample, buccal swab or any other normal tissue obtained from an individual.

The target region of interest may optionally be amplified using any convenient technique, for example PCR.

The region of interest is then analysed for the presence of a marker of heterozygosity. A preferred method of analysis is to test the individual against a panel of markers of heterozygosity using the amplification refractory mutation system (ARMS). Other convenient methods include direct sequencing; cloning and sequencing; heteroduplex analysis methods such as denaturing gradient gel electrophoresis (DGGE) or DHPLC, and enzymatic or chemical mismatch cleavage; in situ hybridisation based methods such as FISH; comparative genome hybridisation (CGH); mini-sequencing; spectral karyotyping (SKY); and hybridisation based methods, including solid phase chip-based techniques. Each of these techniques is well known in the art. Many current methods for the detection of allelic variation (i.e. LOH) are reviewed by Nollau et al., Clin. Chem. 43, 1114–1120, 1997; and in standard textbooks, for example "Laboratory Protocols for Mutation Detection", Ed. by U. Landegren, Oxford University Press, 1996 and "PCR", 2$^{nd}$ Edition by Newton & Graham, BIOS Scientific Publishers Limited, 1997.

The invention has a significant number of uses. These include identification of novel gene sequences; delineation of the sequence of acquired mutations required for neoplasia; including identification of early genetic events associated with the initiation and progression of cancer; early identification of disease caused by acquired genetic change, optionally in association with an inherited variation; identification of changes in the expression of alleles in relation to disease states/therapeutic interventions; identification of novel therapeutic intervention points in a disease process; and identification of gene amplification.

The amplification primers and detection polynucleotides used in the method of the invention may be conveniently packaged with instructions and appropriate packaging and sold as a kit. The kit may also comprise suitable endonucleases (i.e resolvases such as T4 endonuclease VII or T7 endonuclease I) or mismatch binding proteins (i.e Mut S), optionally conjugated to magnetic beads or other separable support, to facilitate enzymatic removal of heteroduplexes.

The invention will now be illustrated but not limited by reference to the following Examples and Figures in which.

The graphs show how the initial difference in the relative proportions of the two alleles is amplified by one or more rounds of heteroduplex formation and removal. Key: open circles represent allele a, solid circles represents allele b. Dashed line represents expected values of alleles a and b at equal frequency allowing for sample removal.

EXAMPLE 1

Detection of Nucleic Acid Sequence Loss Using Physical Heteroduplex Separation Method 1) Identification of a Polymorphic Marker of Allelic Heterozygosity Within the LOCI of Interest Using ARMS™ Allele Specific Amplification Genomic DNA from white blood cells is purified and 5–500 ng is amplified in allele a and b ARMS™ allele specific amplification reactions. A suitable target region is that containing the A/G polymorphism in intron 1 (96 bases upstream from exon 2) of the PTEN gene. When an individual is a germ-line heterozygote for the polymorphism under investigation, diagnostic amplification products will be produced by both ARMS reactions. The detection of amplification products will be accomplished by either post-PCR electrophoresis or real-time analysis using a technique such as Molecular Beacons or Scorpions™ or DHPLC. If the individual is found to be an a/b heterozygote (i.e. with the PTEN example, an A/G heterozygote), then this polymorphism will be used as the marker for subsequent AI (LOH) detection.

2) Amplification of the DNA Region Containing the Polymorphism

DNA (5–500 ng) from both the normal (eg blood—see 1 above) and the clinical (eg paraffin embedded, frozen or fresh tissue) samples are amplified in separate PCR reactions designed to generate ~100–300 bp amplicon which contains a polymorphic site identified in (1)(i.e. the PTEN polymorphism in intron 1). Successful amplification is confirmed by electrophoretic analysis of an aliquot (0.1 volume) of the reaction mix.

3) Amplification of the Difference in Allele Frequency Ratio by One or More Rounds of Heteroduplex Formation and Removal i) Formation of allele a/b heteroduplexes The PCR products in the aliquot from (2) are denatured by heating at 94° C. for 2 min. Heteroduplexes of allele a and b products are formed by cooling to 37° C. over a period of 1 to 2 min. It has been reported that under such conditions, a single base-pair mismatch does not significantly affect the efficiency of heteroduplex formation, relative to homoduplexes (Oka et al., 1994, Nucleic Acids Research 22, 1541–1547). It may be preferable to allow annealing to occur over a greater length of time (up to 1 hour or more).

ii) Removal of heteroduplexes by DHPLC

A Wave™ Fragment Analysis System (Transgenomics Ltd.) DHPLC apparatus can be used.

An aliquot (0.2–0.4 volumes) of the amplification mix (which has been subjected to heteroduplex formation) is applied to a DHPLC column. Unincorporated amplification primers do not have to be removed prior to DHPLC analysis.

Typically chromatographic conditions for separation of homo and heteroduplexes employ a column temperature of 50–60° C. and a 0.1M TEAA mobile phase containing 12.5% AcNi (increasing to 25% over a period of 5 minutes; flow rate ~1 ml/minute). Chromatographic peaks (detected by absorbance at 260 nm) corresponding to aa, bb, and ab, ba duplexes are resolved and column fractions containing the homoduplexes are collected (total volume ~500 μl). The purified fraction volume is reduced to ~10 μl by centrifugal micro-concentration (AMICON Inc.) and the process of heteroduplex formation and removal is repeated.

iii) Quantitation of relative amounts of homoduplexes

The on-line UV detection system will enable direct quantitation of the relative amounts of aa and bb homoduplexes after each round of the process. This could be further refined by employing laser-induced fluorescence to detect labelled PCR products, thus increasing the sensitivity of peak detection and quantitation.

iv) Repeated rounds of heteroduplex formation and removal

Depending on the quantitation values detected in (iii), the heteroduplex depleted reaction mixture may then be subjected to the heteroduplex formation and removal process described above. The process may be repeated one or more times depending on the sensitivity required.

The ratio of allele a:allele b, generated by the DNA originally amplified from normal tissue (ie frequency allele a=allele b), should remain constant irrespective of how many rounds of heteroduplex formation and removal have been performed. In contrast, if the tumour DNA contained AI (eg allele a=40% and b=60%), then the relative ratio of a:b will progressively decrease after each successive round of heteroduplex formation and removal. The number of rounds of this process required to permit detection of AI will depend on the frequency of AI in the sample and the relative efficiency of heteroduplex formation and removal.

EXAMPLE 2

Detection of Nucleic Acid Sequence Loss Using Enzymatic Heteroduplex Separation Method Steps (1), (2) and (3i) from Example 1 are repeated. Prior to step 3(i) it may be necessary to remove unincorporated amplification primers. This may be conveniently performed as follows:

An aliquot (0.2 volumes) of each reaction mix from Example 1 step (2) is treated with 1 unit of commercially available *E. coli* exonuclease 1 (Amersham Pharmacia Biotech) in order to degrade unincorporated amplification primers (Vaughan & McCarthy, 1998, Nucleic Acids Research, 26, 810–815). The exonuclease is subsequently inactivated by heating at 80° C. for 15 min.

Example 2, Step 3 (ii) Enzymatic removal of Heteroduplexes

The following two approaches for the selective removal of heteroduplexes are particularly suitable for use in the method of the invention:

(a) The *E. coli* protein, MutS, binds to regions of double-stranded DNA containing a single mismatched base-pair (Wagner el al, op. cit.). This protein has been conjugated to magnetic beads and is commercially available (Gene Check, Colorado, USA). After annealing, the mismatched heteroduplexes are bound by MutS-beads and separated from homoduplexes using a magnet. The supernatant containing the homoduplexes is then transferred to a fresh tube.

(b) Bacteriophage resolvases, eg T4 endonuclease VII and T7 endonuclease I, enzymatically cleave both strands of DNA at the site of a mismatched base-pair (Mashall et al., 1995, Nature Genetics, 9, 177–183). The addition of resolvase to the annealing reaction will result in the cleavage of mismatched heteroduplexes.

4) Measurement of the Relative Frequency of Alleles a and b by ARMS™ Allele Specific Amplification The relative frequencies of alleles a and b in reaction mix aliquots which have been removed prior to and after each round of heteroduplex formation/removal (ie step 3) can be determined by real-time quantitative PCR combined with Beacons detection (as described in WO95/13399) or Scorpions™ detection (as described in PCT/GB98/0352 1, Zeneca Ltd). Each aliquot is amplified in two separate (allele a and b specific) ARMS allele specific amplification reactions (as described in EP-0332435, Zeneca Ltd) and the respective cycle thresholds (Ct) determined.

The cycle threshold is the first round of amplification (i.e. PCR) at which a signal (derived from the amplification detection system), measurable above the background level, is detected. This value is dictated by the initial amount of allele specific template present.

EXAMPLE 3

Oligonucleotide Model System

The following oligonucleotide model system demonstrates that the instant invention is capable of detecting polymorphisms in nucleic acid fragments by amplifying the initial difference in allele ratio.

Four distinct 30-mer oligonucleotides tailed at their 5'-end with either dinitrophenol (DNP), digoxigenin (DIG) or biotin were purchased from Oswel Research Products Ltd. (Southampton University, England).

Oligo 1 (SEQ ID No. 1) 5'-DNP-GTACTGGTGGAGGAGTCTATTTGATAGTGA-3'

Oligo 2 (SEQ ID No. 2) 5'-biotin-TCACTATCAAATAGAGTCCTCCACCAGTAC-3'

Oligo 3 (SEQ ID No. 3) 5'-DIG-GTACTGGTGGAGGACTCTATTTGATAGTGA-3'

Oligo 4 (SEQ ID No. 4) 5'-biotin-TCACTATCAAATAGACTCCTCCACCAGTAC-3'

Figure 3:
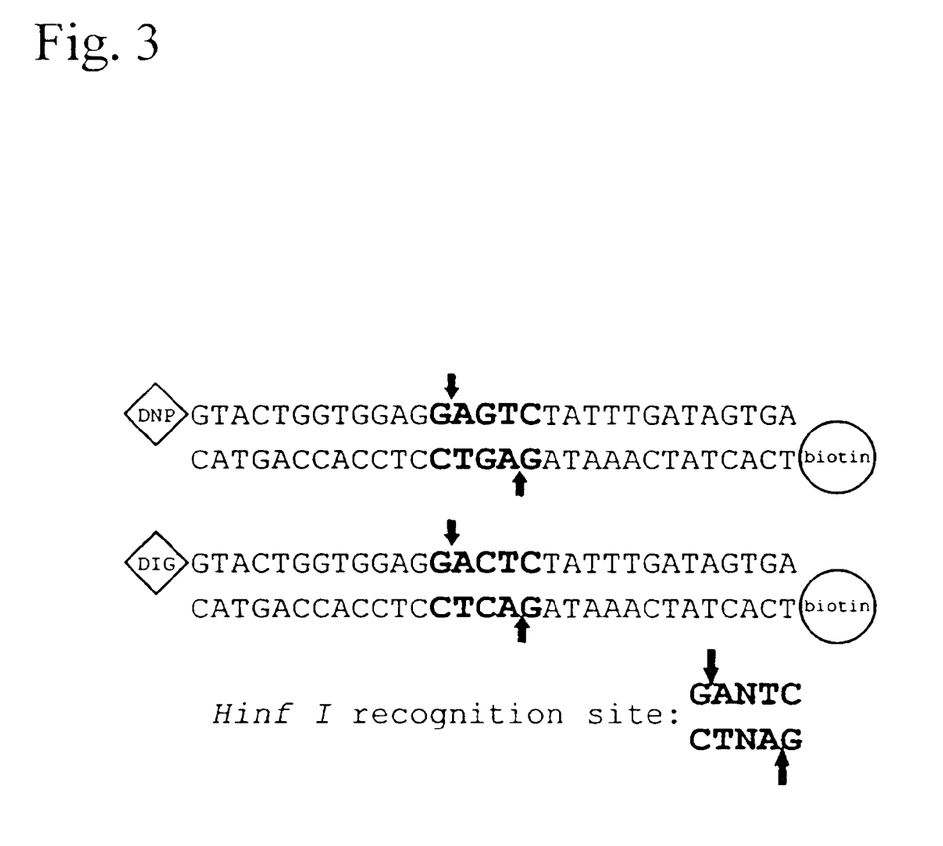
FIG. 3 Shows the two different heteroduplex molecules generated by mixing oligonucleotides 1 with 2 (duplex G, top), and 3 with 4 (duplex C, bottom) to form dinitrophenol (DNP) and digoxigenin (DIG) labelled HinfI resistant molecules (SEQ ID NOS: 1–4).

Two different heteroduplex molecules identical in sequence except for a central base were prepared by mixing equal quantities of oligonucleotides 1 with 2, and 3 with 4 (see FIG. 3) to form dinitrophenol (DNP) and digoxigenin (DIG) labelled HinfI resistant duplexes. The oligos were mixed and allowed to anneal at ambient temperature (in 1xbuffer A: 10 mM Tris-HCl (pH 8.3), 50 mM KCl, 1.2 mM $MgCl_2$, 0.01% v/v gelatin). Mis-match G (oligos 1 and 2) and C (oligos 3 and 4) duplexes (each at 5 pmol/µl) thus formed were employed in the process described below:

1. Duplexes G and C were combined to generate the following proportions: G:C=50:50 and 60:40 (20 pmol total duplex in buffer A; 50 µl total volume)
2. The mixture was heated to 94° C. for 1 min and allowed to cool to ambient temperature (An aliquot ($1/10^{th}$) was removed to provide time 0 ELISA values)
3. The remainder was made up to 50 µl with restriction buffer and enzyme and then digested with 10 units of HinfI (GIBCO BRL) for 90 min @ 37° C. An aliquot ($1/10^{th}$) was then removed for time 1 ELISA values. [note: At each stage the mixture was maintained at 50 µl]
4. Steps 2 (denaturation/annealing) and 3 (restriction digestion) were repeated. An aliquot was removed after each of these for time 2 or 3 or 4 etc. ELISA values (depending on the number of step 2+3 iterations).

ELISA Detection

Each aliquot was made up to 200 µl with PBS, divided between 2 streptavidin-coated microtitre wells and incubated for 60 min @ 37° C. Bound duplexes were incubated with either anti-DNP (Sigma) or anti-DIG (Roche Diagnostics) alkaline phosphatase antibody (30 min @ 37° C.) before addition of p-nitrophenol phosphate (0.5 mg/ml) substrate. After 10 min, the optical densities of the colorimetric reactions were determined at 405 nm.

Figure 4:
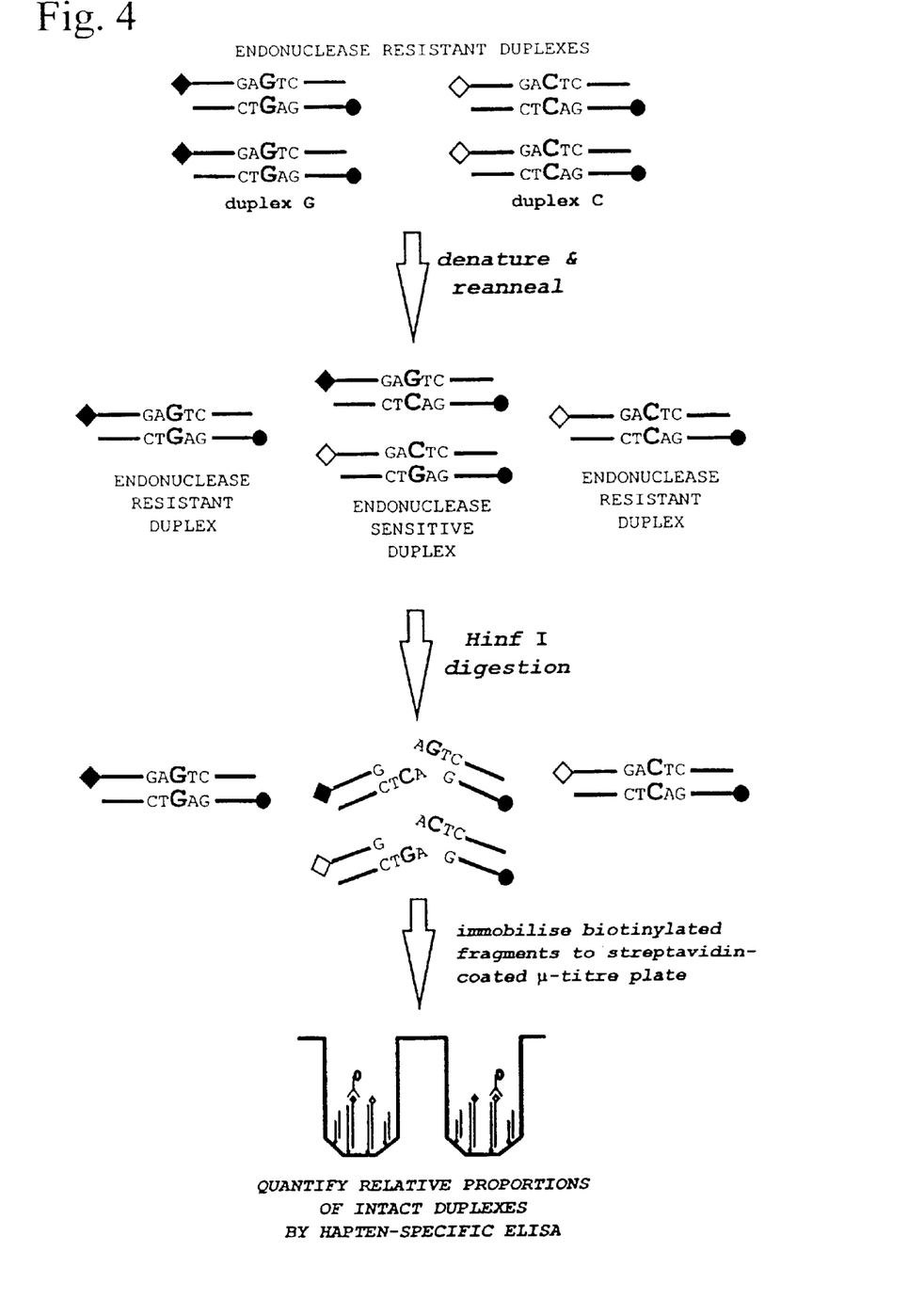
FIG. 4 Illustrates the oligonucleotide model system of Example 3.

The method employed is depicted in FIG. 4.

Figure 5:
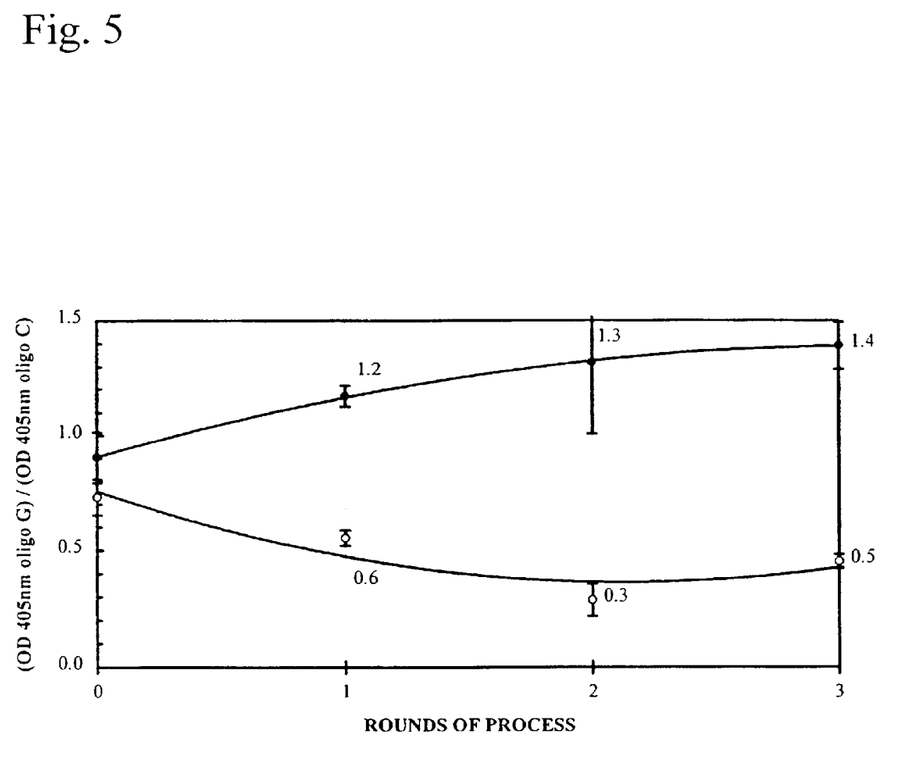
FIG. 5 Depicts the results obtained from Example 3. The graphs show how the initial difference in the relative proportions of the two alleles is amplified by one or more rounds of heteroduplex formation and removal. Key: open circles represent 50:50 ratio of duplex G:C, solid circles represents 60:40 ratio of duplex G:C.

FIG. 5 shows the effect of the above process on the relative proportions of G and C duplexes when the original ratios were 50:50 (open circle) and 60:40 (solid circle), respectively. As can be seen, an initial 1.5 fold imbalance in duplex frequencies was amplified 3 fold after three rounds of the process. If the model were 100% efficient, a 26 fold amplification would have been expected. However, the cleavage of matched oligo duplexes by HinfI has been demonstrated to proceed with at best 80% efficiency. Thus, even if every other step of the process occurred with 100% efficiency, amplification of the initial 1.5 fold imbalance would not be expected to exceed a factor of 6.

This model system exemplifies the method of the invention. As an indicator of assay sensitivity, the oligo model system result for the 60:40 allelic ratio is calculated to correspond to a clinical sample containing approximately 30% tumour cells (containing LOH).

What is claimed is:

1. A method for detecting allelic imbalance (AI) in sample nucleic acid, which method comprises providing multiple copies of a target nucleic acid region present in the sample, the target nucleic acid region comprising a marker of heterozygosity;

separating multiple copies of the target nucleic acid region into individual strands;

reannealling the individual strands under conditions which permit the formation of homoduplexes and heteroduplexes;

removing the heteroduplexes formed; and subjecting the remaining homoduplexes to the above steps of separation, reannealing and heteroduplex removal one or more times so that any difference in the initial ratio of allelic variants is amplified, thereby detecting the presence or absence of AI by reference to any difference in allele ratio.

2. A method for detecting allelic imbalance (AI) in sample nucleic acid, which method comprises providing multiple copies of a target nucleic acid region present in the sample, the target nucleic acid region comprising a marker of heterozygosity;

separating multiple copies of the target nucleic acid region into individual strands;

reannealling the individual strands under conditions which permit the formation of homoduplex and heteroduplex molecules;

subjecting the duplex nucleic acid molecules formed to denaturing high performance liquid chromatography (DHPLC) under conditions which permit the separation of heteroduplex molecules from homoduplex molecules; and subjecting the homoduplex molecules to the above steps of separation, reannealing, and DHPLC one or more times so that any difference in the initial ratio of allelic variants is amplified, thereby detecting the presence or absence of AI by reference to any difference in allele ratio.

3. A method as claimed in claim 1 or 2, wherein the marker of heterozygosity is present within a gene selected from: adenomatous polyposis coli (APC), phosphatase and tensin homolog (PTEN), tumour protein 53 (p53), deleted in colorectal carcinoma (DCC), mannose-6-phosphate/linsulin-like growth factor II receptor (M6P/IGF-II receptor), retinoblastoma 1 (RB1), Wilm's tumour 1 (WT1), neurofibromatosis 1 (NF1), neurofibromatosis 2 (NF2), tuberous sclerosis 1 (TSC1), tuberous sclerosis 2 (TSC2), deleted in pancreatic carcinoma 4 (DPC4), breast cancer gene 1 (BRCA1), breast cancer gene 2 (BRCA2), mutS homolog 2 (MSH2), mutL homolog 1 (MLH1), von Hippel Lindau (VHL), cyclin-dependent kinase inhibitor 2A (CDKN2A), homolog of drosophilia patched gene (PTCH), multiple endocrine neoplasia 1 (MEN1), myelocytomatosis viral oncogene homolog (MYC), Abelson marine leukemia viral oncogene homolog (ABL), rat sarcoma oncogene-Kirsten ($RAS_K$), rat sarcoma oncogene-w ($RAS_W$), myeloblastosis viral oncogene homolog (MYB), erythroblastic leukemia viral oncogene homolog 2 (ERBA), myelocytomatosis viral oncogene homolog—neuroblastoma derived (MYCN), and myelocytomatosis viral oncogene homolog—lung carcinoma derived (MYCL).

4. A method as claimed in claim 1 or 2, wherein the marker of heterozygosity is a single nucleotide polymorphism or an insertion or deletion.

5. A method as claimed in claim 1 or 2, wherein the multiple copies of the target nucleic acid region are provided by amplification.

6. A method as claimed in claim 1 or 2, wherein the multiple copies of the target sequence have a thermostable region incorporated therein to promote the formation of stable heteroduplexes.

7. A method as claimed in claim 6, wherein the thermostable region is a guanine-cytosine (GC) clamping sequence that has been incorporated into the design of the PCR primers used to amplify the nucleic acid regions of interest.

8. A method as claimed in claim 1 or 2, wherein the target nucleic acid region is from 30 to 2000 nucleotides in length.

9. A method as claimed in claim 1 or 2, wherein the nucleic acid strand separation is by thermal means.

10. A method as claimed in claim 1 or 2, wherein the heteroduplexes formed are removed by applying the homoduplex and heteroduplex mixture to a stationary reverse phase support and eluting the heteroduplexes.

11. A method as claimed in claim 1 or 2, wherein the steps of separation, reannealing, and heteroduplex removal are repeated between 1 and 15 times.

12. A method as claimed in claim 1 or 2, wherein the difference in allele ratio is determined by a mutation quantitation technique.

13. A method as claimed in claim 12, wherein the mutation quantitation technique is allele specific amplification.

14. A method as claimed in claim 2, wherein the DHPLC instrument includes an on-line detection system that determines the difference in allele ratio.

15. A method as claimed in claim 1 or 2, wherein the heteroduplexes formed are removed by exposing the homoduplex and heteroduplex mixture to one or more mammalian or bacterial endonucleases which recognizes and cleaves the heteroduplexes at mismatched bases.

16. A method as claimed in claim 1 or 2, wherein the heteroduplexes formed are removed by exposing the homoduplex and heteroduplex mixture to one or more prokaryotic or eukaryotic mismatch binding proteins which selectively bind to mismatch-containing heteroduplexes and remove the protein/DNA complexes formed.

17. A method as claimed in claim 4, wherein the marker of heterozygosity is an insertion or a deletion of between 1 and 10 nucleotides in length.

18. A method as claimed in claim 5, wherein the amplification is by the polymerase chain reaction (PCR).

* * * * *

UNITED STATES PATENT AND TRADEMARK OFFICE
CERTIFICATE OF CORRECTION

PATENT NO.    : 6,586,181 B1
DATED         : July 1, 2003
INVENTOR(S)   : Fox et al.

It is certified that error appears in the above-identified patent and that said Letters Patent is hereby corrected as shown below:

Column 5,
Line 20, change "he" to -- the --; and change "$RAS_K$" to -- $RAS^K$ --;
Line 21, change "$RAS_W$" to -- $RAS^W$ --;

Column 7,
Line 32, change "4449" to -- 44-49 --;

Column 8
Line 20, change "a frequency" to -- a=frequency --;

Column 12,
Line 1, change "Allele" to -- Allelic --;
Line 24, change "5 minutes" to -- ~5 minutes --;

Column 14,
Line 14, change "v/v" to -- w/v --.

Column 17,
Line 32, change "$(RAS_K)$" to -- $(RAS^K)$ --.

Signed and Sealed this

Sixth Day of April, 2004

JON W. DUDAS
*Acting Director of the United States Patent and Trademark Office*

SEQUENCE LISTING

<160> NUMBER OF SEQ ID NOS: 4

<210> SEQ ID NO 1
<211> LENGTH: 30
<212> TYPE: DNA

```
<213> ORGANISM: Artificial Sequence
<220> FEATURE:
<223> OTHER INFORMATION: Oligonucleotide tailed at 5' end with
      dinitrophenol
<220> FEATURE:
<221> NAME/KEY: misc_feature
<222> LOCATION: (1)..(1)
<223> OTHER INFORMATION: n=dinitrophenol-g

<400> SEQUENCE: 1
ntactggtgg aggagtctat ttgatagtga                                    30

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide tailed at 5' end with biotin
<220> FEATURE:
<221> NAME/KEY: misc_feature
<222> LOCATION: (1)..(1)
<223> OTHER INFORMATION: n=biotin-t

<400> SEQUENCE: 2
ncactatcaa atagagtcct ccaccagtac                                    30

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide tailed at 5' end with
      digoxigenin
<220> FEATURE:
<221> NAME/KEY: misc_feature
<222> LOCATION: (1)..(1)
<223> OTHER INFORMATION: n=digoxigenin-g

<400> SEQUENCE: 3
ntactggtgg aggactctat ttgatagtga                                    30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide tailed at 5' end with biotin
<220> FEATURE:
<221> NAME/KEY: misc_feature
<222> LOCATION: (1)..(1)
<223> OTHER INFORMATION: n=biotin-t

<400> SEQUENCE: 4
ncactatcaa atagactcct ccaccagtac                                    30
```